US008829188B2

(12) United States Patent
Hoge et al.

(10) Patent No.: US 8,829,188 B2
(45) Date of Patent: Sep. 9, 2014

(54) FLUOROALKYLFLUOROPHOSPHORANE ADDUCTS

(75) Inventors: Berthold Theo Hoge, Bielefeld (DE); Anne Julia Bader, Bielefeld (DE); Nikolai (Mykola) Ignatyev, Duisburg (DE); Michael Schulte, Bischofsheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/823,750

(22) PCT Filed: Aug. 30, 2011

(86) PCT No.: PCT/EP2011/004354
§ 371 (c)(1),
(2), (4) Date: Mar. 15, 2013

(87) PCT Pub. No.: WO2012/041431
PCT Pub. Date: Apr. 5, 2012

(65) Prior Publication Data
US 2013/0178628 A1    Jul. 11, 2013

(30) Foreign Application Priority Data
Sep. 27, 2010 (EP) .................................. 10010828
Sep. 27, 2010 (EP) .................................. 10010829

(51) Int. Cl.
*C07F 9/58* (2006.01)
*C07F 9/535* (2006.01)
*C07F 9/54* (2006.01)

(52) U.S. Cl.
CPC ................. *C07F 9/581* (2013.01); *C07F 9/535* (2013.01); *C07F 9/5442* (2013.01)
USPC .............................................. 546/21; 568/16

(58) Field of Classification Search
None
See application file for complete search history.

(56) References Cited

U.S. PATENT DOCUMENTS

| 6,264,818 | B1 | 7/2001 | Heider et al. |
| 7,094,328 | B2 | 8/2006 | Ignatyev et al. |
| 8,211,277 | B2 | 7/2012 | Ignatyev et al. |
| 2004/0171879 | A1* | 9/2004 | Ignatyev et al. ............. 562/808 |
| 2010/0004461 | A1 | 1/2010 | Ignatyev et al. |
| 2012/0264946 | A1 | 10/2012 | Ignatyev et al. |

FOREIGN PATENT DOCUMENTS

| DE | 19846636 A1 | 4/2000 |
| WO | 03002579 A1 | 1/2003 |
| WO | 2008092489 A1 | 8/2008 |
| WO | 2011072810 A1 | 6/2011 |

OTHER PUBLICATIONS

International Search Report for PCT/EP2011/004354 dated Jan. 18, 2012.
Kampa et al. "The Synthesis of Tris(perfluoroalkyl)-phosphanes" Angewandte Chemie (International Ed. In English) vol. 34, No. 11, [1995], pp. 1241-1244.
Peter G. M. Wuts, Theodora W. Greene "Greene's Protective Groups in Organic Synthesis, 4th Edition" Wiley-Interscience (Dec. 2006) p. 279, p. 420.

* cited by examiner

*Primary Examiner* — Janet L Andres
*Assistant Examiner* — Timothy R Rozof
(74) *Attorney, Agent, or Firm* — Millen, White, Zelano & Branigan, P.C.

(57) ABSTRACT

The invention relates to fluoroalkylfluorophosphorane adducts and the use thereof for masking OH groups in organic compounds.

20 Claims, No Drawings

FLUOROALKYLFLUOROPHOSPHORANE ADDUCTS

The invention relates to perfluoroalkylfluorophosphorane adducts and the use thereof for masking OH groups in organic compounds.

Fluoroalkylfluorophosphoranes, in particular perfluoroalkylfluorophosphoranes, are strong Lewis acids which react very well with nucleophiles. WO 2008/092489 discloses, for example, the reaction of 1-ethyl-3-methylimidazolium chloride with tris(pentafluoroethyl)difluorophosphorane in acetonitrile, where the ionic liquid 1-ethyl-3-methylimidazolium tris(pentafluoroethyl)difluorochlorophosphate is formed.

However, the reaction of fluoroalkylfluorophosphoranes, in particular perfluoroalkylfluorophosphoranes, with oxygen-containing nucleophiles generally results in complex mixtures of compounds.

However, there continues to be a need in the area of the synthesis of chemical compounds to use fluoroalkylfluorophosphoranes, in particular perfluoroalkylfluorophosphoranes, as starting material also for the reaction with oxygen-containing nucleophiles.

Surprisingly, it has been found that the reactivity and thus the Lewis acidity of fluoroalkylfluorophosphoranes, in particular perfluoroalkylphosphoranes, can be controlled in a targeted manner by preparing adducts with suitable Lewis bases. These adducts are excellent starting materials for the reaction with oxygen-containing nucleophiles, and defined compounds and not complex mixtures are formed in the reaction.

The invention accordingly relates firstly to the compounds of the formula I

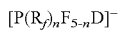  I, where $R_f$ in each case, independently of one another, denotes a straight-chain or branched fluoroalkyl group having 1 to 8 C atoms, n denotes 1, 2 or 3 and D denotes a Lewis base which contains at least one N atom, O atom or at least one P atom and the at least one N, O or P atom has a free electron pair or which contains at least one N—C(=O) group which coordinates to the P atom via the oxygen, and/or tautomers or stereoisomers, including mixtures thereof in all ratios.

A straight-chain or branched fluoroalkyl group having 1 to 8 C atoms is a partially fluorinated or perfluorinated straight-chain or branched alkyl group having 1 to 8 C atoms, i.e. in the case of a perfluorinated alkyl group all H atoms of this alkyl group have been replaced by F. In the case of a partially fluorinated alkyl group having 1 to 8 C atoms, the alkyl group has at least one F atom, 1, 2, 3 or 4 H atoms are present and the other H atoms of this alkyl group have been replaced by F. Known straight-chain or branched alkyl groups are methyl, ethyl, propyl, isopropyl, n-butyl, sec-butyl, tert-butyl, n-pentyl, n-hexyl, n-heptyl or n-octyl. Preferred examples of the partially fluorinated straight-chain or branched alkyl group $R_f$ are CF$_3$—CHF—CF$_2$—, CF$_2$H—CF$_2$—, CF$_3$—CF$_2$—CH$_2$—, CF$_3$—CF$_2$—CH$_2$—CH$_2$— or CF$_3$—CF$_2$—CF$_2$—CF$_2$—CF$_2$—CF$_2$—CH$_2$—CH$_2$—.

A straight-chain or branched perfluoroalkyl group having 1 to 8 C atoms is, for example, trifluoromethyl, pentafluoroethyl, heptafluoropropyl, heptafluoroisopropyl, n-nonafluorobutyl, sec-nonafluorobutyl, tert-nonafluoro-butyl, dodecafluoropentyl, 1-, 2- or 3-trifluoromethyloctafluorobutyl, 1,1-, 1,2- or 2,2-bis(trifluoromethyl)pentafluoropropyl, 1-pentafluoroethylhexafluoropropyl, n-tridecafluorohexyl, n-pentadecafluoroheptyl or n-heptadecafluorooctyl. Preferred examples of the perfluorinated alkyl group $R_f$ are pentafluoroethyl, heptafluoropropyl, heptafluoroisopropyl, nonafluorobutyl, sec-nonafluorobutyl or tert-nonafluorobutyl.

The substituents $R_f$ in the compounds of the formula I are preferably, in each case independently of one another, straight-chain or branched perfluoroalkyl groups having 1 to 8 C atoms, particularly preferably, in each case independently of one another, perfluoroalkyl groups having 1 to 4 C atoms, very particularly preferably, in each case independently of one another, perfluoroalkyl groups having 2 to 4 C atoms, especially very particularly preferably pentafluoroethyl or nonafluorobutyl. The substituents $R_f$ in the compounds of the formula I are preferably identical.

The number n denotes 1, 2 or 3. n preferably stands for the number 2 or 3, very particularly preferably for the number 3.

Preferred Lewis bases D which have the desired properties are selected, for example, from the group aromatic amine, which has basic properties, dialkyl ether, aromatic or aliphatic tertiary phosphine, dialkylformamide, dialkylacetamide or N-alkyl-2-pyrrolidone, where the said alkyl groups have, in each case independently of one another, 1 to 8 C atoms.

A straight-chain or branched alkyl group having 1 to 8 C atoms is, for example, methyl, ethyl, isopropyl, propyl, butyl, sec-butyl or tert-butyl, furthermore pentyl, 1-, 2- or 3-methylbutyl, 1,1-, 1,2- or 2,2-dimethylpropyl, 1-ethylpropyl, n-hexyl, n-heptyl or n-octyl.

Preferred aromatic amines are, for example, pyridine, morpholine, piperazine, imidazole, oxazole or thiazole, each of which may be substituted by alkyl groups having 1 to 8 C atoms or dialkylamino groups, which each have, independently of one another, 1 to 8 C atoms. The aromatic amine is particularly preferably selected from the group pyridine, 4-methylpyridine or 4-dimethylaminopyridine.

A preferred dialkyl ether is diethyl ether.

Triphenylphosphine oxide (phenyl$_3$P=O) or trimethyl phosphate (methyl$_3$PO$_4$) can also be employed as Lewis base D.

Preferred aromatic or aliphatic tertiary phosphines are, for example, triphenylphosphine, diphenylmethylphosphine, trimethylphosphine, triethylphosphine, tri-i-propylphosphine, tributylphosphine, trihexylphosphine, tricyclohexylphosphine. A particularly preferred tertiary aliphatic phosphine is trimethylphosphine.

Preferred dialkylformamides are, for example, dimethylformamide, diethylformamide, dipropylformamide. A particularly preferred dialkylformamide is dimethylformamide.

Preferred dialkylacetamides are, for example, dimethylacetamide, diethylacetamide or dipropylacetamide.

Preferred N-alkyl-2-pyrrolidones are, for example, N-methyl-2-pyrrolidone, N-ethyl-2-pyrrolidone, N-propyl-2-pyrrolidone or N-butyl-2-pyrrolidone.

Particularly preferred Lewis bases D are selected, for example, from the group aromatic amine or dialkylformamide, as described above.

Very particularly preferred Lewis bases are 4-dimethylaminopyridine or dimethylformamide. An especially very particularly preferred Lewis base is 4-dimethylaminopyridine.

The invention is furthermore directed to a process for the preparation of the compounds of the formula I, as described above or as preferably described, characterised in that a fluoroalkylfluorophosphorane of the formula II

  II, where $R_f$ in each case, independently of one another, denotes a straight-chain or branched fluoroalkyl group having 1 to 8 C atoms and n denotes 1, 2 or 3, is reacted with a Lewis base D, where the Lewis base contains at least one N atom, O atom or at least one P atom and the at least one N, O or P atom has a free electron pair, or contains at least one N—C(=O) group which coordinates to the P atom via the oxygen.

For the preferred meanings of the substituents $R_f$, the number n and the Lewis base D, the comments as described above apply.

The preparation of perfluoroalkylfluorophosphoranes of the formula II can be carried out by conventional methods known to the person skilled in the art. These compounds are preferably prepared by electrochemical fluorination of suitable starting compounds [V. Y. Semenii et al., 1985, *Zh. Obshch. Khim.* 55 (12): 2716-2720; N. V. Ignatyev, P. Sartori, 2000, *J. Fluorine Chem.* 103: 57-61; WO 00/21969].

Fluoroalkylfluorophosphoranes can be obtained by free-radical addition of dialkyl phosphites, $(RO)_2P(O)H$ or phosphines onto fluoroolefins [N. O. Brace, *J. Org. Chem.*, 26 (1961), p. 3197-3201; P. Cooper, R. Fields, R. N. Haszeldine, *J. Chem. Soc., Perkin I*, 1975, p. 702-707; G. M. Burch, H. Goldwhite, R. N. Haszeldine, *J. Chem. Soc.*, 1963, p. 1083-1091] or to fluoro-alkylolefins see P. Kirsch, *Modern Fluoroorganic Chemistry*, WILEY-VCH, 2004, p. 174], following a chlorination/fluorination or an oxidative fluorination. The reaction of the phosphorane of the formula II with the Lewis base, as described above or as preferably described, is carried out at temperatures of 0 to 80° C., preferably 15 to 30° C., in the presence of an organic solvent and in a water-free atmosphere.

Suitable solvents here are acetonitrile, dioxane, dichloromethane, dimethoxyethane, dimethyl sulfoxide, tetrahydrofuran or dialkyl ethers, for example diethyl ether or methyl t-butyl ether.

The Lewis base D is preferably employed in excess, i.e. the added molar amount of Lewis base is greater than the molar amount of starting compound of the formula II, as described above.

The fluoroalkylfluorophosphorane adducts of the formula I, in particular the perfluoroalkylfluorophosphorane adducts of the formula I, can be isolated. However, they can also be reacted with nucleophiles in the reaction mixture of the preparation process.

The structure of the compounds of the formula I can be interpreted by way of example as follows, which describes the stereoisomeric variability of the position of the F and fluoroalkyl groups on the P. Base here denotes the Lewis base D.

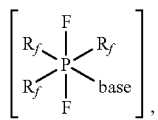  Ia

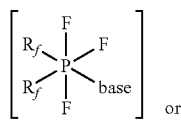  Ib or

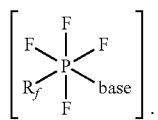  Ic

In particular, the compounds of the formula I, as described above or as preferably described, can be reacted with nucleophiles which contain an oxygen atom.

The reaction of the compounds of the formula I, as described above, with water (HOH), an alcohol (ROH) or a carboxylic acid (RCOOH), for example, results in the preparation of defined compounds having a corresponding phosphate anion $[P(R_f)_nF_{5-n}X]^-$, where the proton liberated is scavenged and stabilised by the Lewis base, and X denotes OH, OR or OC(O)R, i.e. denotes the radical of the alcohol employed or of the carboxylic acid, and $R_f$ and the number n have a meaning indicated above. Examples of such reactions are indicated in the example part.

However, the compounds of the formula I are also eminently suitable for masking OH groups of an organic compound.

The invention is therefore furthermore directed to a method for masking at least one OH group of an organic compound, characterised in that this compound is reacted with a compound of the formula I, as described above or as preferably described.

The choice of the organic compound is unrestricted, so long as the compound carries at least one OH group which is able to react with the compound of the formula I.

The organic compound containing at least one OH group is preferably an aliphatic or aromatic alcohol containing at least one OH group or an oligomeric or polymeric compound containing at least one OH group.

Suitable aliphatic or aromatic alcohols containing at least one OH group are methanol, ethanol, butanol, hexanol, octanol, allyl alcohol, phenol, hydroquinone, 1,2-ethanediol, 1,3-propanediol, 1,4-butanediol, 1,2,3-propanetriol (glycerol), oxo compounds, such as, for example, glycerol aldehyde, or further polyols, i.e. compounds containing more than 3 OH groups.

The term polyols is applied to a group of organic compounds which contain a plurality of hydroxyl groups, here at least three OH groups. Polyols may have either a linear or cyclic structure.

From the group of the aliphatic or aromatic alcohols, so-called polyols are particularly preferred.

The polyols include, for example, D-threitol, L-threitol, erythrol, D-arabinitol, L-arabinitol, adonitol, xylitol, D-sorbitol, D-mannitol or galactitol. Furthermore, the term polyols also encompasses the group of the carbohydrates, including monosaccharides, disaccharides, oligosaccharides and polysaccharides or polyhydroxy acids thereof.

Monosaccharides are, for example, erythrose, threose, ribose, arabinose, xylose, lyxose, allose, altrose, glucose, mannose, gulose, idose, galactose, talose, dihydroxyacetone, erythrulose, ribulose, xylulose, psicose, fructose, sorbose, tagatose, including all stereoisomeric forms, in particular the D and L forms, and alpha- or beta-anomers.

Disaccharides are, for example, sucrose, lactose, trehalose, maltose or cellobiose.

Oligosaccharides are carbohydrates consisting of at least three carbohydrate units, for example raffinose or acarbose.

Polysaccharides are characterised in that they are composed of many carbohydrate units which form a macromolecule. Starch, glycogen or cellulose are, for example, polysaccharides.

The polyols also include polyester-polyols or polyether-polyols.

The organic compound containing at least one OH group is preferably a polyol or a polyethylene glycol.

Polyols can be described by the sub-formula $[-CH_2CHOH-]_n$, having molecular weights between 5000 and 200,000, for example in polyvinyl alcohol, or as copolymer with other polymers, for example as poly-(vinyl alcohol-co-ethylene) $[(CH_2CH_2)_x[CH_2CHOH]_y$ having molecular weights between 5000 and 200,000.

Polyethylene glycol is liquid or solid, depending on the chain length, and can be described by the formula $H[-O-(CH_2)_2-O]_m-H$. Polyethylene glycols up to a chain length m of 600 monomer units are liquid. Solid from a chain length of 600 monomer units.

Polyols are particularly preferably masked. In the case of polyols, the masking of the OH groups can take place completely or partially, depending on the amount of compounds of the formula I employed, as described above or as preferably described. Through specific control of the amount of compounds of the formula I employed, a corresponding proportion of OH groups in the polyol can be specifically masked. The remaining OH groups are furthermore accessible to further derivatisation.

The following working examples are intended to explain the invention without limiting it. The invention can be carried out correspondingly throughout the range claimed. Possible variants can also be derived starting from the examples. In particular, the features and conditions of the reactions described in the examples can also be applied to other reactions which are not shown in detail, but fall within the scope of protection of the claims.

EXAMPLES

The substances obtained are characterised by means of mass spectrometry, elemental analysis and NMR spectroscopy. NMR spectra are recorded using the Avance III 300 spectrometers, from Bruker, Karlsruhe. Acetone-d6 is used in a capillary as lock substance. The referencing is carried out using external reference: TMS for $^1H$ and $^{13}C$ spectra; $CCl_3F-$ for $^{19}F$ and 80% $H_3PO_4-$ for $^{31}P$ spectra.

Example 1

Preparation of $[P(C_2F_5)_3F_2(dmap)]$

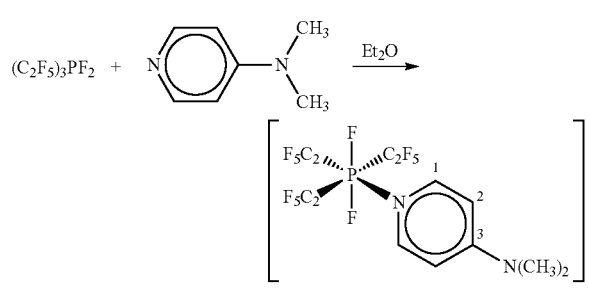

2.8 g (22.9 mmol) of 4-(dimethylamino)pyridine are initially introduced in 100 ml of diethyl ether, and 12.2 g (28.6 mmol) of $(C_2F_5)_3PF_2$ are slowly added. After stirring for 15 minutes, volatile constituents are removed in vacuo, leaving a colourless solid.

Yield (based on DMAP): 12.1 g (97%). Melting point: 150-153° C.

$^{31}P$, δ, ppm=−144.5, t, quin, t, $^1J(PF)$=986 Hz, $^2J(PF_{cis})$= 107 Hz,
$^2J(PF_{trans})$=97 Hz, assignment $[P(C_2F_5)_3F_2(dmap)]$ in diethyl ether.

$^{19}F$, δ, ppm=−80.4 m (trans-$CF_3$); −81.6 m (cis-$CF_3$); −99.4 d (PF), $^1J(PF)$=986 Hz, −111.5 m (br) (cis-$CF_2$), −115.3 d,m (trans-$CF_2$), $^2J(PF)$=95 Hz. Measurement in $CDCl_3$.

$^1H$, δ, ppm=3.2 s ($N(CH_3)_2$), 6.7 d (H2), $^3J(HH)$=7 Hz, 8.4 m (br) (H1) Measurement in $CDCl_3$.

$^{13}C$, δ, ppm=38.6$^a$ s ($-N(CH_3)_2$), 105.9$^a$ s (C1), 116.7$^b$ m ($-CF_2CF_3$), 118.2$^b$ m ($-CF_2CF_3$), 138.9$^a$ m (C2), 156.1$^a$ s (C3). Measurement in CDCl3.

$^1\{^1H\}^b\{^{19}F\}$

Elemental analysis data of $[P(C_2F_5)_3F_2(dmap)]$

|  | N | C | H |
|---|---|---|---|
| calculated | 5.11 | 28.48 | 1.84 |
| experimental | 4.91 | 28.63 | 1.67 |

Example 2

Preparation of $[PPh_4][P(C_2F_5)_3F_2OH]$

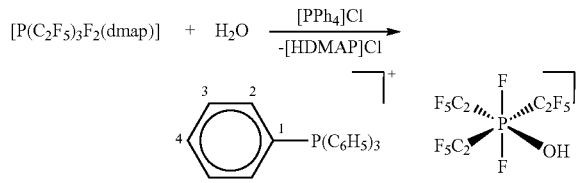

0.96 g (1.75 mmol) of $[P(C_2F_5)_3F_2(dmap)]$ are initially introduced in ether, and excess water is added. After stirring for 30 minutes, 0.66 g (1.75 mmol) of $[PPh_4]Cl$, dissolved in 2 ml of water, are added, and the mixture is again stirred for 20 minutes. The aqueous phase is subsequently separated off, and the organic phase is extracted three times with water. The organic phase is dried in vacuo, leaving a colourless solid as residue. Yield (based on $[P(C_2F_5)_3F_2(dmap)]$: 1.29 g (94%). Melting point: 139° C.

$^{31}P$-NMR spectroscopic data of $[PPh_4][P(C_2F_5)_3F_2OH]$ in $CD_3CN$ $^{31}P$, δ, ppm=23.2 s ($[PPh_4][P(C_2F_5)_3F_2OH]$), −148.3 t, sept ($[PPh_4][P(C_2F_5)_3F_2OH]$), $^1J(PF)$=845 Hz, $^2J(PF)$=86 Hz.

$^{19}F$ ($CD_3CN$), δ, ppm=−80.1 m (trans-$CF_3$); −81.2 m (cis-$CF_3$); −86.6 d, m (PF), $^1J(PF)$=846 Hz, −114.1 d(cis,trans-$CF_2$), $^2J(PF)$=86 Hz.

$^1H$ ($CD_3CN$), δ, ppm=5.1 t, d ($[P(C_2F_5)_3F_2OH]$), $^3J(FH)$= 14 Hz, $^2J(PH)$=3 Hz, 7.8-8.1 m ($[PPh_4]^+$).

$^{13}C$ ($CD_3CN$), δ, ppm=118.5$^a$ d (C1), $^1J(PC)$=90 Hz, 119.1$^b$ m ($-CF_2CF_3$), 120.7$^b$ m ($-CF_2CF_3$), 130.3$^a$ d (C2), $^2J(PC)$= 13 Hz, 134.7$^a$ d (C3), $^3J(PC)$=10 Hz, 135.4$^a$ d (C4), $^4J(PC)$=3 Hz.

$^a\{^1H\}^b\{^{19}F\}$

Elemental analysis data of $[PPh_4][P(C_2F_5)_3F_2OH]$

|  | C | H |
|---|---|---|
| calculated | 46.05 | 2.71 |
| experimental | 46.40 | 2.79 |

Example 3

Preparation of [HDMAP][(C$_2$F$_5$)$_3$PF$_2$OC(O)CH$_3$]

[P(C$_2$F$_5$)$_3$F$_2$(dmap)] + H$_3$C−C(=O)−OH ⟶ [HDMAP]$^+$ [(C$_2$F$_5$)$_3$PF$_2$OC(O)CH$_3$]$^-$ 0.52 g (0.96 mmol) of [P(C$_2$F$_5$)$_3$F$_2$(dmap)] are initially introduced in dichloromethane. 0.19 g (3.17 mmol) of acetic acid are added at room temperature, and the reaction mixture is stirred for 3 hours. Volatile constituents are subsequently removed in vacuo, leaving a colourless solid. Yield (based on [P(C$_2$F$_5$)$_3$F$_2$(dmap)]): 0.54 g (93%)

$^{31}$P-NMR spectroscopic data of [HDMAP][P(C$_2$F$_5$)$_3$F$_2$OC(O)CH$_3$] in CD$_3$CN

| δ, ppm | Multiplicity | J[Hz] | Assignment |
|---|---|---|---|
| −146.3 | t, quin, t | $^1$J(PF) = 915<br>$^2$J(PF$_{cis}$) = 103<br>$^2$J(PF$_{trans}$) = 84 | [P(C$_2$F$_5$)$_3$F$_2$OC(O)CH$_3$]$^-$ |

$^{19}$F-NMR spectroscopic data of [HDMAP][(C$_2$F$_5$)$_3$PF$_2$OC(O)CH$_3$] in CD$_3$CN

| δ, ppm | Multiplicity | J[Hz] | Assignment | Integral |
|---|---|---|---|---|
| −80.2 | m | — | trans-CF$_3$ | 1 |
| −81.8 | m | — | cis-CF$_3$ | 2 |
| −86.9 | d, m | $^1$J(PF) = 923 | PF | 0.6 |
| −115.3 | d, m | $^2$J(PF) = 85 | trans-CF$_2$ | — |
| −116.0 | d, m | $^2$J(PF) = 103 | cis-CF$_2$ | — |

$^1$H-NMR spectroscopic data of [HDMAP][P(C$_2$F$_5$)$_3$F$_2$OC(O)CH$_3$] in CD$_3$CN

| δ, ppm | Multiplicity | J[Hz] | Assignment | Integral |
|---|---|---|---|---|
| 1.9 | s | — | —OC(O)CH$_3$ | 1.6 |
| 3.2 | s | — | —N(CH$_3$)$_2$ | 3 |
| 6.9 | d | $^3$J(HH) = 7 | H1 | 1 |
| 7.9 | d | $^3$J(HH) = 7 | H2 | 1 |

$^{13}$C-NMR spectroscopic data of [HDMAP][P(C$_2$F$_5$)$_3$F$_2$OC(O)CH$_3$] in CD$_3$CN

| δ, ppm | Multiplicity | J[Hz] | Assignment |
|---|---|---|---|
| 23.3 [a] | s | — | —OC(O)CH$_3$ |
| 39.6 [a] | s | — | —N(CH$_3$)$_2$ |
| 107.1 [a] | s | — | C1 |
| 116.7 [b] | m | — | —CF$_2$CF$_3$ |
| 120.0 [b] | m | — | —CF$_2$CF$_3$ |
| 138.6 [a] | s | — | C2 |
| 157.7 [a] | s | — | C3 |
| 166.3 [a] | d | $^2$J(PC) = 18 | —OC(O)CH$_3$ |

[a] {$^1$H}
[b] {$^{19}$F}

Example 4

Preparation of [HDMAP][P(C$_2$F$_5$)$_3$F$_2$OPh]

[P(C$_2$F$_5$)$_3$F$_2$(dmap)] + PhOH ⟶ [HDMAP]$^+$ [P(C$_2$F$_5$)$_3$F$_2$OPh]$^-$ 0.52 g (0.95 mmol) of [P(C$_2$F$_5$)$_3$F$_2$(dmap)] are initially introduced in diethyl ether. 0.13 g (1.34 mmol) of phenol are added at room temperature, and the reaction mixture is stirred for 12 hours. Two phases form. The solvent is removed in vacuo, leaving a clear, colourless liquid.

$^{31}$P-NMR spectroscopic data of [HDMAP][P(C$_2$F$_5$)$_3$F$_2$OPh] in CD$_3$CN

| δ, ppm | Multiplicity | J[Hz] | Assignment |
|---|---|---|---|
| −147.5 | t, quin, t | $^1$J(PF) = 893<br>$^2$J(PF$_{cis}$) = 98<br>$^2$J(PF$_{trans}$) = 84 | [P(C$_2$F$_5$)$_3$F$_2$OPh]$^-$ |

$^{19}$F-NMR spectroscopic data of [HDMAP][P(C$_2$F$_5$)$_3$F$_2$OPh] in CD$_3$CN

| δ, ppm | Multiplicity | J[Hz] | Assignment | Integral |
|---|---|---|---|---|
| −79.4 | m | — | trans-CF$_3$ | — |
| −80.5 | m | — | cis-CFs | — |
| −85.5 | d, m | $^1$J(PF) = 896 | PF | — |
| −111.5 | d, m | $^2$J(PF) = 97 | cis-CF$_2$ | — |
| −112.7 | d, m | $^2$J(PF) = 79 | trans-CF$_2$ | — |

$^1$H-NMR spectroscopic data of [HDMAP][P(C$_2$F$_5$)$_3$F$_2$OPh] in CD$_3$CN

| δ, ppm | Multiplicity | J[Hz] | Assignment | Integral |
|---|---|---|---|---|
| 3.4 | s | — | —N(CH$_3$)$_2$ | 3 |
| 6.7 | d | $^3$J(HH) = 7 | H1 | 1 |
| 7.1 | m | — | —OC$_6$H$_5$ | 2.2 |
| 8.3 | d | $^3$J(HH) = 7 | H2 | 1 |

$^{13}$C-NMR spectroscopic data of [HDMAP][P(C$_2$F$_5$)$_3$F$_2$OPh] in CD$_3$CN

| δ, ppm | Multiplicity | J[Hz] | Assignment |
|---|---|---|---|
| 39.7 [a] | s | — | —N(CH$_3$)$_2$ |
| 106.9 [a] | s | — | C1 |
| 115.2 [a] | s | — | C5 |
| 118.1 [b] | m | — | —CF$_2$CF$_3$ |
| 119.7 [b] | m | — | —CF$_2$CF$_3$ |
| 120.4 [a] | s | — | C6/7 |
| 128.9 [a] | s | — | C6/7 |
| 138.8 [a] | s | — | C2 |
| 157.0 [a] | s | — | C4 |
| 157.6 [a] | s | — | C3 |

[a] {$^1$H}
[b] {$^{19}$F}

Example 5

Preparation of [HDMAP]$_2$[{P(C$_2$F$_5$)$_3$F$_2$O}$_2$C$_6$H$_4$]

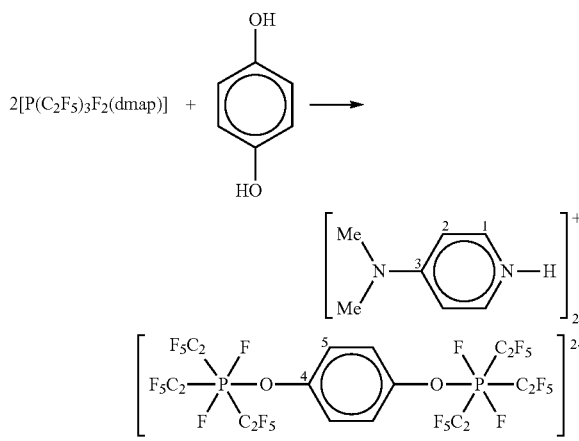

1.11 g (2 mmol) of [P(C$_2$F$_5$)$_3$F$_2$(dmap)] are initially introduced in diethyl ether. 0.11 g (1 mmol) of hydroquinone are added at room temperature, and the reaction mixture is stirred for 4 hours. Volatile constituents are subsequently removed in vacuo, leaving a colourless solid. Yield (based on hydroquinone): 0.85 g (78%).

$^{31}$P-NMR spectroscopic data of [HDMAP]$_2$[{P(C$_2$F$_5$)$_3$F$_2$O}$_2$C$_6$H$_4$] in CD$_3$CN

| δ, ppm | Multiplicity | J[Hz] | Assignment |
|---|---|---|---|
| −148.0 | t, quin, t | $^1$J(PF) = 882<br>$^2$J(PF$_{cis}$) = 96<br>$^2$J(PF$_{trans}$) = 78 | [{P(C$_2$F$_5$)$_3$F$_2$O}$_2$C$_6$H$_4$]$^{2-}$ |

$^{19}$F-NMR spectroscopic data of [HDMAP]$_2$[{P(C$_2$F$_5$)$_3$F$_2$O}$_2$C$_6$H$_4$] in CD$_3$CN

| δ, ppm | Multiplicity | J[Hz] | Assignment | Integral |
|---|---|---|---|---|
| −80.4 | m | — | trans-CF$_3$ | 1 |
| −81.6 | m | — | cis-CF$_3$ | 2 |
| −86.9 | d, m | $^1$J(PF) = 881 | PF | 0.6 |
| −112.9 | d, m | $^2$J(PF) = 98 | cis-CF$_2$ | 1.3 |
| −113.9 | d, m | $^2$J(PF) = 80 | trans-CF$_2$ | 0.7 |

$^1$H-NMR spectroscopic data of [HDMAP]$_2$[{P(C$_2$F$_5$)$_3$F$_2$O}$_2$C$_6$H$_4$] in CD$_3$CN

| δ, ppm | Multiplicity | J[Hz] | Assignment | Integral |
|---|---|---|---|---|
| 3.1 | s | — | —N(CH$_3$)$_2$ | 3 |
| 6.8 | m | — | H5/6 | 0.5 |
| 6.8 | d | $^3$J(HH) = 8 | H1 | 1 |
| 7.9 | d | $^3$J(HH) = 8 | H2 | 1 |

Elemental analysis data of [HDMAP]$_2$[{P(C$_2$F$_5$)$_3$F$_2$O}$_2$C$_6$H$_4$]

| | N | C | H |
|---|---|---|---|
| calculated | 4.67 | 32.07 | 1.51 |
| experimental | 4.73 | 32.40 | 2.26 |

Example 6

Preparation of [HDMAP][P(C$_2$F$_5$)$_3$F$_2$OEt]

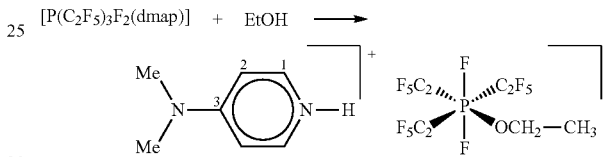

10.6 g (230 mmol) of ethanol are initially introduced in 100 ml of Et$_2$O. 12.5 g (23 mmol) of [P(C$_2$F$_5$)$_3$F$_2$(dmap)] are added at room temperature, and the mixture is stirred for 30 minutes. Volatile substances are subsequently removed overnight in vacuo, leaving a colourless solid. Yield (based on [P(C$_2$F$_5$)$_3$F$_2$(dmap)]): 13.6 g (100%). Melting point: 75-78° C.

$^{31}$P-NMR spectroscopic data of [HDMAP][P(C$_2$F$_5$)$_3$F$_2$OEt] in CD$_3$CN

| δ, ppm | Multiplicity | J[Hz] | Assignment |
|---|---|---|---|
| −149.4 | t, sept | $^1$J(PF) = 869<br>$^2$J(PF) = 88 | [P(C$_2$F$_5$)$_3$F$_2$OC$_2$H$_5$]$^-$ |

$^{19}$F-NMR spectroscopic data of [HDMAP][P(C$_2$F$_5$)$_3$F$_2$OEt] in CD$_3$CN

| δ, ppm | Multiplicity | J[Hz] | Assignment | Integral |
|---|---|---|---|---|
| −80.6 | m | — | trans-CF$_3$ | 1 |
| −81.8 | m | — | cis-CF$_3$ | 2 |
| −94.5 | d | $^1$J(PF) = 869 | PF | 0.6 |
| −113.5 | d, m | $^2$J(PF) = 83 | trans-CF$_2$ | 0.6 |
| −114.4 | d, m | $^2$J(PF) = 86 | cis-CF$_2$ | 1.3 |

$^1$H-NMR spectroscopic data of [HDMAP][P(C$_2$F$_5$)$_3$F$_2$OEt] in CD$_3$CN

| δ, ppm | Multiplicity | J[Hz] | Assignment | Integral |
|---|---|---|---|---|
| 1.1 | t, d | $^3$J(HH) = 7<br>$^4$J(PH) = 1 | —OCH$_2$CH$_3$ | 1.4 |
| 3.2 | s | — | —N(CH$_3$)$_2$ | 3 |

-continued

| δ, ppm | Multiplicity | J[Hz] | Assignment | Integral |
|---|---|---|---|---|
| 4.0 | pseudo-quin | $^3J(PH) = 7$<br>$^3J(HH) = 7$ | —OCH$_2$CH$_3$ | 0.9 |
| 5.3 | s | — | —NH$^+$ | 1 |
| 6.8 | d | $^3J(HH) = 7$ | H1 | 1 |
| 8.0 | d | $^3J(HH) = 7$ | H2 | 1 |

$^{13}$C-NMR spectroscopic data of [HDMAP][P(C$_2$F$_5$)$_3$F$_2$OEt] in CD$_3$CN

| δ, ppm | Multiplicity | J[Hz] | Assignment |
|---|---|---|---|
| 16.0 $^a$ | d | $^3J(CP) = 10$ | —OCH$_2$CH$_3$ |
| 39.6 $^a$ | s | — | (CH$_3$)$_2$N— |
| 61.8 $^a$ | m | — | —OCH$_2$CH$_3$ |
| 107.1 $^a$ | s | — | C1 |
| 118.8 $^b$ | m | — | —CF$_2$CF$_3$ |
| 122.5 $^b$ | m | — | —CF$_2$CF$_3$ |
| 138.5 $^a$ | s | — | C2 |
| 157.9 $^a$ | s | — | C3 |

$^a$ {$^1$H}
$^b$ {$^{19}$F}

Elemental analysis data of [HDMAP][P(C$_2$F$_5$)$_3$F$_2$OEt]

| | N | C | H |
|---|---|---|---|
| calculated | 4.71 | 30.32 | 2.71 |
| experimental | 4.74 | 30.32 | 2.69 |

Example 7

Preparation of [HDMAP][P(C$_2$F$_5$)$_3$F$_2$OCH$_2$CF$_3$]

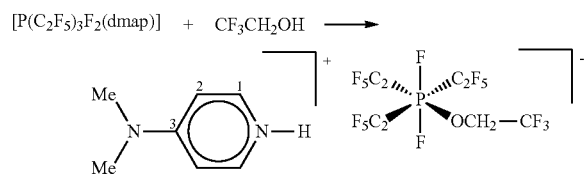

2.5 g (4.5 mmol) of [P(C$_2$F$_5$)$_3$F$_2$(dmap)] are initially introduced in diethyl ether. 0.9 g (9.0 mmol) of trifluoroethanol are added at room temperature, and the reaction mixture is stirred for 12 hours. Volatile constituents are subsequently removed in vacuo, leaving a colourless solid. Yield (based on [P(C$_2$F$_5$)$_3$F$_2$(dmap)]): 2.8 g (95%). Melting point: 91-93° C.

$^{31}$P-NMR spectroscopic data of [HDMAP][P(C$_2$F$_5$)$_3$F$_2$OCH$_2$CF$_3$] in CD$_3$CN

| δ, ppm | Multiplicity | J[Hz] | Assignment |
|---|---|---|---|
| −149.9 | t, sept | $^1J(PF) = 886$<br>$^2J(PF) = 88$ | [P(C$_2$F$_5$)$_3$F$_2$OCH$_2$CF$_3$]$^-$ |

$^{19}$F-NMR spectroscopic data of [HDMAP][P(C$_2$F$_5$)$_3$F$_2$OCH$_2$CF$_3$] in CD$_3$CN

| δ, ppm | Multiplicity | J[Hz] | Assignment | Integral |
|---|---|---|---|---|
| −75.4 | s | — | [P(C$_2$F$_5$)$_3$F$_2$OCH$_2$CF$_3$]$^-$ | 1 |
| −79.6 | m | — | trans-CF$_3$ | 1 |
| −80.8 | m | — | cis-CF$_3$ | 2 |
| −93.8 | d, m | $^1J(PF) = 883$ | PF | 0.5 |
| −112.2 | d, m | — | trans-, cis-CF$_3$ | 2.2 |

$^1$H-NMR spectroscopic data of [HDMAP][P(C$_2$F$_5$)$_3$F$_2$OCH$_2$CF$_3$] in CD$_3$CN

| δ, ppm | Multiplicity | J[Hz] | Assignment | Integral |
|---|---|---|---|---|
| 3.2 | s | — | —N(CH$_3$)$_2$ | 3 |
| 4.4 | quar, d | $^3J(FH) = 9$<br>$^3J(PH) = 4$ | —OCH$_2$CF$_3$ | 1 |
| 6.8 | d | $^3J(HH) = 7$ | H1 | 1 |
| 8.0 | d | — | H2 | 1 |

$^{13}$C-NMR spectroscopic data of [HDMAP][P(C$_2$F$_5$)$_3$F$_2$OCH$_2$CF$_3$] in CD$_3$CN

| δ, ppm | Multiplicity | J[Hz] | Assignment |
|---|---|---|---|
| 39.6 $^a$ | s | — | —N(CH$_3$)$_2$ |
| 64.1 $^a$ | m | — | —OCH$_2$CF$_3$ |
| 106.9 $^a$ | s | — | C1 |
| 118.8 $^b$ | m | — | —CF$_2$CF$_3$ |
| 120.4 $^b$ | m | — | —CF$_2$CF$_3$ |
| 124.5 $^b$ | m | — | —OCH$_2$CF$_3$ |
| 138.9 $^a$ | s | — | C2 |
| 157.7 $^a$ | s | — | C3 |

$^a$ {$^1$H}
$^b$ {$^{19}$F}

Elemental analysis data of [HDMAP][P(C$_2$F$_5$)$_3$F$_2$OCH$_2$CF$_3$]

| | N | C | H |
|---|---|---|---|
| calculated | 4.32 | 27.79 | 2.02 |
| experimental | 4.47 | 28.10 | 1.64 |

Example 8

Preparation of [HDMAP][P(C$_2$F$_5$)$_3$F$_2$ODec]

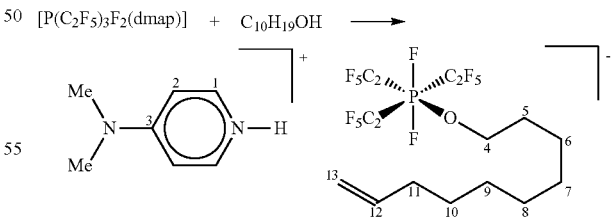

0.69 g (1.25 mmol) of [P(C$_2$F$_5$)$_3$F$_2$(dmap)] are dissolved in Et$_2$O. 0.20 g (1.25 mmol) of 9-decen-1-ol are added at room temperature, and the mixture is stirred for 1.5 hours. The reaction mixture is subsequently dried in vacuo, leaving a clear viscous liquid. Yield (based on [P(C$_2$F$_5$)$_3$F$_2$(dmap)]): 0.88 g (99%). Melting point: <20° C.

$^{31}$P-NMR spectroscopic data of [HDMAP][P(C$_2$F$_5$)$_3$F$_2$ODec] in CDCl$_3$

| δ, ppm | Multiplicity | J[Hz] | Assignment |
|---|---|---|---|
| −147.2 | t, sept | $^1J(PF) = 873$<br>$^1J(PF) = 88$ | $[P(C_2F_5)_3F_2OC_{10}H_{19}]^-$ |

$^{19}$F-NMR spectroscopic data of [HDMAP][P($C_2F_5$)$_3$F$_2$ODec] in CDCl$_3$

| δ, ppm | Multiplicity | J[Hz] | Assignment | Integral |
|---|---|---|---|---|
| −79.7 | m | — | trans-CF$_3$ | 1 |
| −81.0 | m | — | cis-CFs | 2.1 |
| −94.9 | d, m | $^1J(PF) = 876$ | PF | 0.5 |
| −113.0 | d, m | — | cis-, trans-CF$_2$ | 2.1 |

$^1$H-NMR spectroscopic data of [HDMAP][P($C_2F_5$)$_3$F$_2$ODec] in CDCl$_3$

| δ, ppm | Multiplicity | J[Hz] | Assignment | Integral |
|---|---|---|---|---|
| 1.2–1.6 | m | — | H6–H10 | 5.7 |
| 1.5 | t | $^3J(HH) = 7$ | H5 | — |
| 2.0 | quin | $^3J(HH) = 7$ | H11 | 1 |
| 3.2 | s | — | —N(CH$_3$)$_2$ | 3 |
| 3.7 | t | $^3J(HH) = 7$ | H4 | 0.6 |
| 4.9–5.0 | m | — | H13 | 0.9 |
| 5.8 | m | — | H12 | 0.5 |
| 6.7 | d | $^3J(HH) = 7$ | H1 | 1 |
| 7.8 | d | $^3J(HH) = 7$ | H2 | 1 |

$^{13}$C{$^1$H}-NMR spectroscopic data of [HDMAP][P($C_2F_5$)$_3$F$_2$ODec] in CDCl$_3$

| δ, ppm | Multiplicity | J[Hz] | Assignment |
|---|---|---|---|
| 25.7; 28.9;<br>29.0; 29.3;<br>29.4 | s | — | C6–C10 |
| 32.8 | s | — | C5 |
| 33.8 | s | — | C11 |
| 40.0 | s | — | —N(CH$_3$)$_2$ |
| 63.2 | s | — | C4 |
| 107.0 | s | — | C1 |
| 114.1 | s | — | C13 |
| 138.5 | s | — | C2 |
| 139.3 | s | — | C12 |
| 157.4 | s | — | C3 |

Example 9

Preparation of [HDMAP][P($C_2F_5$)$_3$F$_2$OC$_2$H$_4$OH]

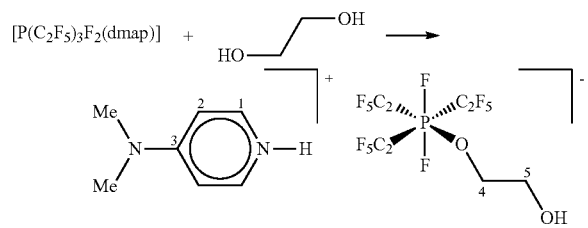

0.60 g (1.1 mmol) of [P(C$_2$F$_5$)$_3$F$_2$(dmap)] are initially introduced in diethyl ether. 0.10 g (1.6 mmol) of ethylene glycol are added at room temperature, and the reaction mixture is stirred for 24 hours. Volatile constituents are subsequently removed in vacuo, leaving a colourless solid. Yield (based on [P(C$_2$F$_5$)$_3$F$_2$(dmap)]): 0.61 g (89%). Melting point: 88° C. (softening of the sample), 91° C. decomposition.

$^{31}$P-NMR spectroscopic data of [HDMAP][P($C_2F_5$)$_3$F$_2$OC$_2$H$_4$OH]

| δ, ppm | Multiplicity | J[Hz] | Assignment |
|---|---|---|---|
| −149.2 | t, sept | $^1J(PF) = 871$<br>$^2J(PF) = 86$ | $[P(C_2F_5)_3F_2OC_2H_4OH]^-$ |

$^{19}$F-NMR spectroscopic data of [HDMAP][P($C_2F_5$)$_3$F$_2$OC$_2$H$_4$OH]

| δ, ppm | Multiplicity | J[Hz] | Assignment | Integral |
|---|---|---|---|---|
| −79.3 | m | — | trans-CF$_3$ | 1 |
| −80.4 | m | — | cis-CFs | 1.8 |
| −93.2 | d, m | $^1J(PF) = 873$ | PF | 0.3 |
| −112.6 | d, m | $^2J(PF) = 83$ | trans-, cis-CF$_2$ | 1.8 |

$^1$H-NMR spectroscopic data of [HDMAP][P($C_2F_5$)$_3$F$_2$OC$_2$H$_4$OH]

| δ, ppm | Multiplicity | J[Hz] | Assignment | Integral |
|---|---|---|---|---|
| 3.2 | s | — | —N(CH$_3$)$_2$ | 3 |
| 3.5 | t | $^3J(HH) = 4$ | H5 | 0.8 |
| 4.0 | pseudo-quar | $^3J(HH) = 4$<br>$^3J(PH) = 4$ | H4 | 0.6 |
| 6.8 | d | $^3J(HH) = 8$ | H1 | 1 |
| 8.0 | d | $^3J(HH) = 8$ | H2 | 1 |

$^{13}$C-NMR spectroscopic data of [H DMAP][P($C_2F_5$)$_3$F$_2$OC$_2$H$_4$OH]

| δ, ppm | Multiplicity | J[Hz] | Assignment |
|---|---|---|---|
| 39.6 [a] | s | — | —N(CH$_3$)$_2$ |
| 62.1 [a] | d | $^2J(PC) = 9$ | C4 |
| 67.8 [a] | s | — | C5 |
| 106.8 [a] | s | — | C1 |
| 116.7 [b] | m | — | —CF$_2$CF$_3$ |
| 120.6 [b] | m | — | —CF$_2$CF$_3$ |
| 138.6 [a] | s | — | C2 |
| 157.6 [a] | s | — | C3 |

[a] {$^1$H}
[b] {$^{19}$F}

Elemental analysis data of [HDMAP][P($C_2F_5$)$_3$F$_2$OC$_2$H$_4$OH]

| | N | C | H |
|---|---|---|---|
| calculated | 4.59 | 29.52 | 2.64 |
| experimental | 4.62 | 29.54 | 2.28 |

Example 10

Preparation of [P(C₂F₅)₃F₂(dmf)]

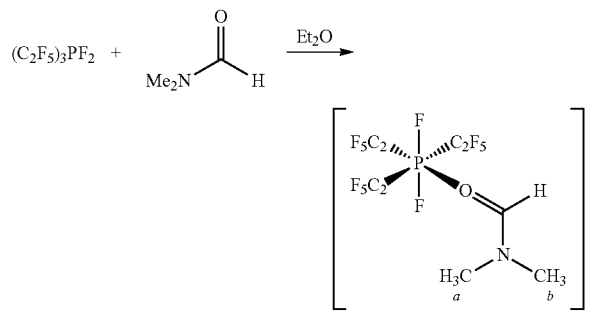

0.12 g (1.7 mmol) of DMF are initially introduced in about 15 ml of diethyl ether, and 1.02 g (2.4 mmol) of $(C_2F_5)_3PF_2$ are added. The reaction mixture is stirred at room temperature for 45 minutes. The solvent and excess $(C_2F_5)_3PF_2$ are subsequently removed in vacuo, leaving a colourless solid. Yield (based on DMF): 0.84 g (99%).

$^{31}$P-NMR spectroscopic data of $[P(C_2F_5)_3F_2(dmf)]$ in DMF

| δ, ppm | Multiplicity | J[Hz] | Assignment |
|---|---|---|---|
| −142.1 | t, t, quin | $^2J(PF) = 960$<br>$J(PF_{trans}) = 87$<br>$^2J(PF_{cis}) = 103$ | $[P(C_2F_5)_3F_2(dmf)]$ |

$^{19}$F-NMR spectroscopic data of $[P(C_2F_5)_3F_2(dmf)]$ in DMF

| δ, ppm | Multiplicity | J[Hz] | Assignment | Integral |
|---|---|---|---|---|
| −81.4 | m | — | trans-CF₃ | 1 |
| −82.4 | m | — | cis-CF₃ | 2 |
| −92.6 | d, m (br) | $^1J(PF) = 947$ | PF | 0.3 |
| −113.8 | m (br) | — | cis-CF₂ | 1 |
| −116.4 | d | $^2J(PF) = 88$ | trans-CF₂ | 0.6 |

$^1$H-NMR spectroscopic data of $[P(C_2F_5)_3F_2(dmf)]$ in DMF

| δ, ppm | Multiplicity | J[Hz] | Assignment | Integral |
|---|---|---|---|---|
| 2.7 | s | — | CH₃ (a) | 1 |
| 3.1 | s | — | CH₃ (b) | 0.9 |
| 8.4 | s | — | $[P(C_2F_5)_3F_2(OCHNMe_2)]$ | 0.3 |

$^{13}$C-NMR spectroscopic data of $[P(C_2F_5)_3F_2(dmf)]$ in DMF

| δ, ppm | Multiplicity | J[Hz] | Assignment |
|---|---|---|---|
| 34.6 [a] | (hidden) | — | CH₃ (a) |
| 39.8 [a] | quar | $^1J(CH) = 143$ | CH₃ (b) |
| 117.0 [b] | d, m | $^1J(CP) = 249$ | —CF₂CF₃ |
| 119.0 [b] | d, m | $^2J(CP) = 30$ | —CF₂CF₃ |
| 163.2 [a] | d | $^1J(CH) = 218$ | $[P(C_2F_5)_3F_2(OCHNMe_2)]$ |

[a] {¹H}
[b] {¹⁹F}

Example 11

Reaction of [P(C₂F₅)₃F₂(dmf)] with H₂O

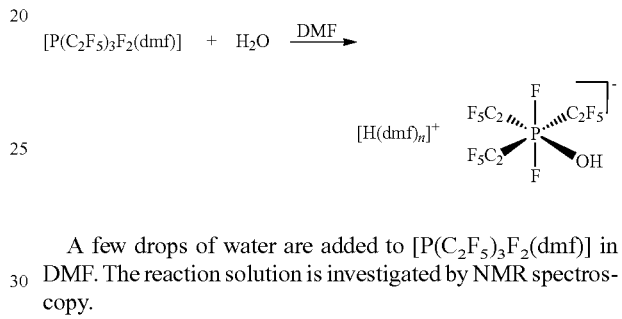

A few drops of water are added to $[P(C_2F_5)_3F_2(dmf)]$ in DMF. The reaction solution is investigated by NMR spectroscopy.

$^{31}$P-NMR spectroscopic data of $[H(dmf)_n][P(C_2F_5)_3F_2OH]$ in Aceton-d₆

| δ, ppm | Multiplicity | J[Hz] | Assignment |
|---|---|---|---|
| −147.9 | t, sept | $^1J(PF) = 847$<br>$^2J(PF) = 86$ | $[H(dmf)_n][P(C_2F_5)_3F_2OH]$ |

$^{19}$F-NMR spectroscopic data of $[H(dmf)_n][P(C_2F_5)_3F_2OH]$ in acetone-d₆

| δ, ppm | Multiplicity | J[Hz] | Assignment | Integral |
|---|---|---|---|---|
| −80.5 | m | — | trans-CF₃ | 1 |
| −81.5 | m | — | cis-CF₃ | 1.9 |
| −87.0 | d, m | $^1J(PF) = 839$ | PF | 0.6 |
| −114.5 | d | $^2J(PF) = 85$ | cis-, trans-CF₂ | 1.9 |

$^1$H-NMR spectroscopic data of $[H(dmf)_n][P(C_2F_5)_3F_2OH]$ in acetone-d₆

| δ, ppm | Multiplicity | J[Hz] | Assignment | Integral |
|---|---|---|---|---|
| 2.7 | s | — | CH₃ (a) | 1.1 |
| 3.0 | s | — | CH₃ (b) | 1 |
| 8.8 | s | — | $[H(OHCNMe_2)_n]$ | — |

Example 12

Reaction of [P(C₂F₅)₃F₂(dmf)] with EtOH

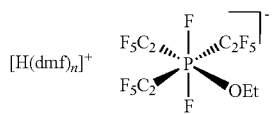

A few drops of ethanol are added to [P(C₂F₅)₃F₂(dmf)] in DMF. The reaction solution is investigated by NMR spectroscopy.

$^{31}$P-NMR spectroscopic data of [H(dmf)$_n$][P(C₂F₅)₃F₂OEt] in DMF

| δ, ppm | Multiplicity | J[Hz] | Assignment |
|---|---|---|---|
| −148.6 | t, pseudo-sept | $^1$J(PF) = 871 | [H(dmf)$_n$][P(C₂F₅)₃F₂OEt] |

$^{19}$F-NMR spectroscopic data of [H(dmf)$_n$][P(C₂F₅)₃F₂OEt] in DMF

| δ, ppm | Multiplicity | J[Hz] | Assignment | Integral |
|---|---|---|---|---|
| −79.2 | m | — | trans-CF₃ | 1 |
| −80.5 | m | — | cis-CF₃ | 1.9 |
| −93.1 | d, m | $^1$J(PF) = 871 | PF | 0.6 |
| −112.3 | d, m | $^2$J(PF) = 83 | trans-CF₂ | — |
| −113.1 | d, m | $^2$J(PF) = 86 | cis-CF₂ | — |

Example 13

Reaction of (C₄F₉)₃PF₂ with DMF

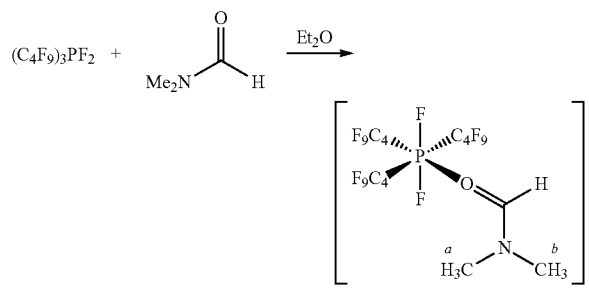

(C₄F₉)₃PF₂ is added to excess DMF. The reaction solution is investigated by NMR spectroscopy.

$^{31}$P-NMR spectroscopic data of [P(C₄F₉)₃F₂(dmf)] in DMF

| δ, ppm | Multiplicity | J[Hz] | Assignment |
|---|---|---|---|
| −135.5 | t, m | $^1$J(PF) = 999<br>$^2$J(PF) = 102 | [P(C₄F₉)₃F₂(dmf)] |

$^{19}$F-NMR spectroscopic data of [P(C₄F₉)₃F₂(dmf)] in DMF $^a$

| δ, ppm | Multiplicity | J[Hz] | Assignment | Integral |
|---|---|---|---|---|
| −82.1 | s | — | CF₃ | — |
| −108.1 – −126.2 | m | — | CF₂ | — |

$^a$ The resonance of the fluorine atoms bonded to the phosphorus atom is covered by other resonances.

$^1$H-NMR spectroscopic data of [P(C₄F₉)₃F₂(dmf)] in DMF

| δ, ppm | Multiplicity | J[Hz] | Assignment | Integral |
|---|---|---|---|---|
| 2.7 | s | — | CH₃ (a) | 0.9 |
| 3.1 | s | — | CH₃ (b) | 1 |
| 8.4 | s | — | [P(C₄F₉)₃F₂(OCHNMe₂)] | 0.3 |

Example 14

Reaction of [P(C₄F₉)₃F₂(dmf)] with EtOH

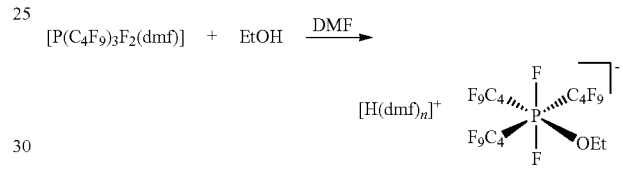

A few drops of ethanol are added to [P(C₄F₉)₃F₂(dmf)] in DMF. The reaction mixture is investigated by NMR spectroscopy.

$^{31}$P-NMR spectroscopic data of [H(dmf)$_n$][P(C₄F₉)₃F₂OEt] in DMF

| δ, ppm | Multiplicity | J[Hz] | Assignment |
|---|---|---|---|
| −143.3 | t, m | $^1$J(PF) = 903<br>$^2$J(PF) = 88 | [H(dmf)$_n$][P(C₄F₉)₃F₂OEt] |

$^{19}$F-NMR spectroscopic data of H[P(C₄F₉)₃F₂OEt].nDMF in DMF

| δ, ppm | Multiplicity | J[Hz] | Assignment | Integral |
|---|---|---|---|---|
| −82.3 | m | — | CF₃ | — |
| −92.3 | d, m | $^1$J(PF) = 899 | PF | — |
| −109.6 – −127.6 | m | — | CF₂ | — |

Example 15

Preparation of [P(C₂F₅)₂F₃(dmf)]

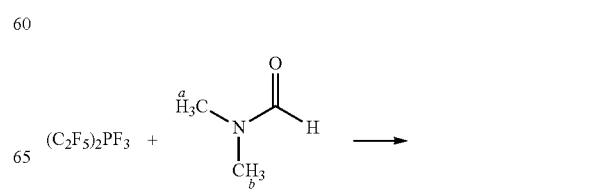

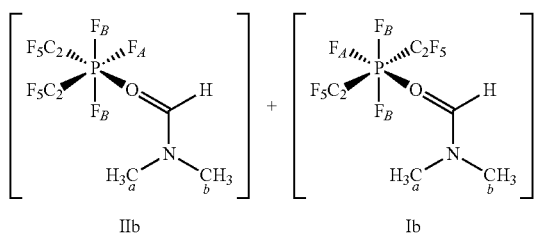

0.09 g (1.2 mmol) of DMF are initially introduced in about 15 ml of diethyl ether, and 1.5 mmol of $(C_2F_5)_2PF_3$ are condensed on. The reaction mixture is investigated by NMR spectroscopy. Two conformers, IIb and Ib, form on slow thawing. IIb is converted into Ib within a few hours at room temperature. After stirring at room temperature for 30 minutes, the solvent is removed in vacuo, leaving a colourless solid. Yield (based on DMF): 0.47 g (97%).

$^{31}$P-NMR spectroscopic data of the two conformers of $[P(C_2F_5)_2F_3(dmf)]$ in DMF

| δ, ppm | Multiplicity | J[Hz] | Assignment |
|---|---|---|---|
| −146.6 | d, t, quin, d | $^1J(PF_A) = 847$ | $[P(C_2F_5)_2F_3(dmf)]$ (IIb) |
|  |  | $^1J(PF_B) = 922$ |  |
|  |  | $^2J(PF) = 95$ |  |
|  |  | $^3J(PH) = 7$ |  |
| −148.7 | d, t, quin | $^1J(PF_A) = 947$ | $[P(C_2F_5)_2F_3(dmf)]$ (Ib) |
|  |  | $^1J(PF_B) = 986$ |  |
|  |  | $^2J(PF) = 108$ |  |

$^{19}$F-NMR spectroscopic data of the two conformers of $[P(C_2F_5)_2F_3(dmf)]$ in DMF

| δ, ppm | Multiplicity | J[Hz] | Assignment | Integral |
|---|---|---|---|---|
| −58.7 | d, m | $^1J(PF_A) = 848$ | $PF_A$ (IIb) | 0.3 |
| −69.1 | d, m | $^1J(PF_A) = 948$ | $PF_A$ (Ib) | 0.8 |
| −74.9 | d, d, m | $^1J(PF_B) = 987$ | $PF_B$ (Ib) | 1.7 |
|  |  | $^2J(F_BF_A) = 45$ |  |  |
| −76.2 | d, d, m | $^1J(PF_B) = 922$ | $PF_B$ (IIb) | 0.7 |
|  |  | $^2J(F_BF_A) = 46$ |  |  |
| −82.7 | m | — | $CF_3$ (IIb) | 1.0 |
| −83.4 | m | — | $CF_3$ (IIb)/$CF_3$ (Ib) | 6.2 |
| −117.5 | d, m | $^2J(PF) = 95$ | $CF_2$ (IIb) | 0.6 |
| −118.7 | d, d, t, m | $^2J(PF) = 108$ | $CF_2$ (Ib) | 3.4 |
|  |  | $^3J(FF_A) = 10$ |  |  |
|  |  | $^3J(FF_B) = 11$ |  |  |
| −119.5 | d, m | $^2J(PF) = 93$ | $CF_2$ (IIb) | 0.6 |

$^1$H-NMR spectroscopic data of the two conformers of $[P(C_2F_5)_2F_3(dmf)]$ in DMF

| δ, ppm | Multiplicity | J[Hz] | Assignment | Integral |
|---|---|---|---|---|
| 2.1 | s | — | $CH_3$ (a) (IIb) | 0.3 |
| 2.1 | s | — | $CH_3$ (a) (Ib) | 1 |
| 2.4 | s | — | $CH_3$ (b) (IIb) | 0.2 |
| 2.5 | s | — | $CH_3$ (b) (Ib) | 1 |
| 7.8 | s | — | $[P(C_2F_5)_2F_3(OCHNMe_2)]$ (Ib) | 0.3 |
| 10.5 | s (br) | — | $[P(C_2F_5)_2F_3(OCHNMe_2)]$ (IIb) | — |

$^{13}$C-NMR spectroscopic data of the two conformers of $[P(C_2F_5)_2F_3(dmf)]$ in DMF

| δ, ppm | Multiplicity | J[Hz] | Assignment |
|---|---|---|---|
| 35.0[a] | (hidden) | — | $CH_3$ (a) (Ib) |
| 40.0[a] | quar | $^1J(CH) = 144$ | $CH_3$ (b) (Ib) |
| 115.5[b] | d, m | $^1J(CP) = 329$ | $-CF_2CF_3$ |
| 119.4[b] | d, m | $^2J(CP) = 32$ | $-CF_2CF_3$ |
| 163.4[a] | d, t | $^1J(CH) = 214$ | $[P(C_2F_5)_2F_3(OCHNMe_2)]$ (Ib) |

[a] {$^1$H}
[b] {$^{19}$F}

Example 16

Reaction of $[P(C_2F_5)_2F_3(dmf)]$ with $H_2O$

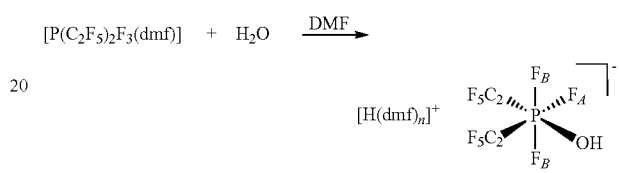

Water is condensed onto a solution of $[P(C_2F_5)_2F_3(dmf)]$ (Ib) in DMF at −196° C. The reaction mixture is warmed to room temperature and investigated by NMR spectroscopy.

$^{31}$P-NMR spectroscopic data of $[H(dmf)_n][P(C_2F_5)_2F_3OH]$ in DMF

| δ, ppm | Multiplicity | J[Hz] | Assignment |
|---|---|---|---|
| −154.4 | d, t, quin | $^1J(PF_A) = 910$ | $[H(dmf)_n][P(C_2F_5)_2F_3OH]$ |
|  |  | $^1J(PF_B) = 926$ |  |
|  |  | $^2J(PF) = 108$ |  |

$^{19}$F-NMR spectroscopic data of $[H(dmf)_n][P(C_2F_5)_2F_3OH]$ in DMF

| δ, ppm | Multiplicity | J[Hz] | Assignment | Integral |
|---|---|---|---|---|
| −63.2 | d, m | $^1J(PF) = 910$ | $PF_A$ | 0.6 |
| −76.0 | d, d, m | $^1J(PF) = 926$ | $PF_B$ | 2 |
|  |  | $^2J(FF) = 46$ |  |  |
| −83.4 | d, t | $^3J(PF) = 11$ | $CF_3$ | 6 |
|  |  | $^3J(FF) = 7$ |  |  |
| −118.9 | d, quar | $^2J(PF) = 103$ | $CF_2$ | 4 |
|  |  | $^3J(FF) = 10$ |  |  |

Example 17

Reaction of $[P(C_2F_5)_2F_3(dmf)]$ with EtOH

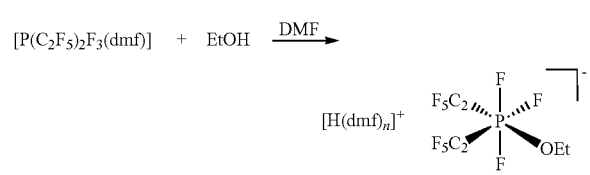

Ethanol is condensed onto a solution of $[P(C_2F_5)_2F_3(dmf)]$ (Ib) in DMF at −196° C. The reaction mixture is warmed to room temperature and investigated by NMR spectroscopy.

$^{31}$P-NMR spectroscopic data of [H(dmf)$_n$][P(C$_2$F$_5$)$_2$F$_3$OEt] in DMF

| δ, ppm | Multiplicity | J[Hz] | Assignment |
|---|---|---|---|
| −152.6 | d, t, quin | $^1$J(PF$_A$) = 860<br>$^1$J(PF$_B$) = 876<br>$^2$J(PF) = 94 | [H(dmf)$_n$][P(C$_2$F$_5$)$_2$F$_3$OEt] |

$^{19}$F-NMR spectroscopic data of [H(dmf)$_n$][P(C$_2$F$_5$)$_2$F$_3$OEt] in DMF

| δ, ppm | Multiplicity | J[Hz] | Assignment | Integral |
|---|---|---|---|---|
| −57.2 | d, m | $^1$J(PF) = 860 | PF$_A$ | 1 |
| −78.5 | d, d, m | $^1$J(PF) = 876<br>$^2$J(FF) = 47 | PF$_B$ | 2.5 |
| −83.5 | d, t | $^3$J(PF) = 13<br>$^3$J(FF) = 7 | CF$_3$ | 8 |
| −119.3 | d, d, t | $^2$J(PF) = 94<br>$^3$J(FF$_A$) = 16<br>$^3$J(FF$_B$) = 8 | CF$_2$ | 5 |

Example 18

Reaction of (C$_2$F$_5$)$_3$PF$_2$·DMAP with 2-[2-(aminoethyl)-amino]ethanol

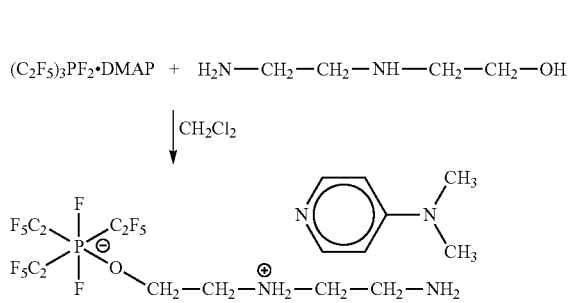

Experimental Procedure:

6.50 g (11.86 mmol) of (C$_2$F$_5$)$_3$PF$_2$·DMAP in 80 ml of dichloromethane are initially introduced in a 100 ml Schlenk flask under protective gas, and 1.23 g (11.86 mmol) of 2-[2-(aminoethyl)amino]ethanol are added dropwise to the solution at 0° C. After the addition, the ice bath is removed, and the mixture is stirred at RT overnight. $^{19}$F- and $^{31}$P-NMR reaction checks are recorded next morning.

The reaction solution is then freed from CH$_2$Cl$_2$ and all volatile constituents in vacuo, leaving a slightly yellow powder.

Crude yield: 7.71 g (91.7% of theory)

If the reaction is carried out in DMF instead of in CH$_2$Cl$_2$, another isomer forms in which the two F atoms on the phosphorus are different.

NMR data: in CD$_2$Cl$_2$

| Nucleus | δ (ppm) | Splitting | Coupling | Assignment |
|---|---|---|---|---|
| $^{31}$P | −148.9 | t, sept | $^1$J$_{PF}$ = 879<br>$^2$J$_{PF}$ = 87 | —PF$_2$(C$_2$F$_5$)$_3$ |
| $^{19}$F | −94.6 | d | $^1$J$_{PF}$ = 879 | —PF$_2$(CF$_2$CF$_3$)$_3$ |
| | −81.2 | m | | —PF$_2$(CF$_2$CF$_3$)$_3$ (6F) |
| | −80.0 | m | | —PF$_2$(CF$_2$CF$_3$)$_3$ (3F) |
| | −113.4 | m | | —PF$_2$(CF$_2$CF$_3$)$_3$ (4F) |
| | −113.7 | m | | —PF$_2$(CF$_2$CF$_3$)$_3$ (2F) |
| $^1$H | 8.02 | d | $^3$J$_{HH}$ = 7.0 | DMAP (2H) |
| | 6.67 | d | $^3$J$_{HH}$ = 7.0 | DMAP (2H) |
| | 5.61 | s, br | | 4H |
| | 4.19 | m | | 2H |
| | 3.13 | s | | DMAP (6H) |
| | 2.89 | m | | 6H |
| $^{13}$C | 155.9 | s | | DMAP |
| | 144.1 | s | | DMAP |
| | 106.8 | s | | DMAP |
| | 63.2 | m | | —O—CH$_2$— |
| | 48.9 | d | $^3$J$_{CP}$ = 8.7 | —O—CH$_2$—CH$_2$—N— |
| | 48.1 | s | | H$_2$N—(CH$_2$)$_2$—N— |
| | 39.2 | s | | DMAP |
| | 38.2 | s | | H$_2$N—(CH$_2$)$_2$—N— |

Example 19

Reaction of (C$_2$F$_5$)$_3$PF$_2$·DMAP with ethyl 6-hydroxyhexanoate

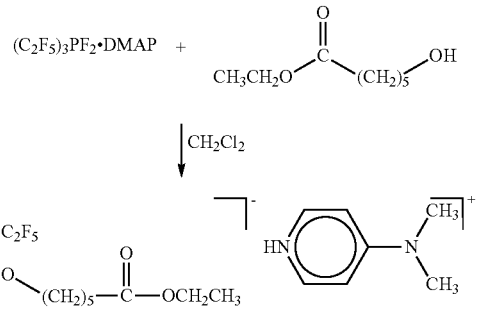

Experimental Procedure:

3.30 g (6.02 mmol) of (C$_2$F$_5$)$_3$PF$_2$·DMAP in 40 ml of dichloromethane are initially introduced in a 100 ml Schlenk flask under protective gas, and 0.96 g (6.02 mmol) of ethyl 6-hydroxyhexanoate is added dropwise to the solution at 0° C. After the addition, the ice bath is removed, and the mixture is stirred at RT overnight. $^{19}$F- and $^{31}$P-NMR reaction checks are recorded next morning.

The reaction solution is freed from CH$_2$Cl$_2$ and all volatile constituents in vacuo, leaving an orange oil.

Crude yield: 4.2 g (98.6% of theory)

NMR data: in CD$_2$Cl$_2$

| Nucleus | δ (ppm) | Splitting | Coupling | Assignment |
|---|---|---|---|---|
| $^{31}$P | −147.9 | t, sept | $^1$J$_{PF}$ = 870<br>$^2$J$_{PF}$ = 89 | —PF$_2$(C$_2$F$_5$)$_3$ |
| $^{19}$F | −94.4 | d | $^1$J$_{PF}$ = 870 | —PF$_2$(CF$_2$CF$_3$)$_3$ |
| | −80.9 | m | | —PF$_2$(CF$_2$CF$_3$)$_3$ (6F) |
| | 79.8 | m | | —PF$_2$(CF$_2$CF$_3$)$_3$ (3F) |
| | −113.0 | m | | —PF$_2$(CF$_2$CF$_3$)$_3$ (4F) |
| | −113.3 | m | | —PF$_2$(CF$_2$CF$_3$)$_3$ (2F) |
| $^1$H | 7.92 | d | $^3$J$_{HH}$ = 7.0 | DMAP (2H) |
| | 6.80 | d | $^3$J$_{HH}$ = 7.0 | DMAP (2H) |
| | 4.13 | q | | —O—CH$_2$CH$_3$ (2H) |
| | 3.99 | q | | —O—(CH$_2$)$_4$—CH$_2$— (2H) |
| | 3.26 | s | | DMAP (6H) |
| | 2.32 | t | $^3$J$_{HH}$ = 7.4 | —O—(CH$_2$)$_4$—CH$_2$— |
| | 1.62 | m | | C(O)— (2H) |

-continued

| Nucleus | δ (ppm) | Splitting | Coupling | Assignment |
|---|---|---|---|---|
|  | 1.53 | m |  | —O—$(CH_2)_4$—$CH_2$— (2H) |
|  | 1.32 | m |  | —O—$(CH_2)_4$—$CH_2$— (2H) |
|  | 1.27 | t | $^3J_H = 7.0$ | —O—$(CH_2)_4$—$CH_2$— (2H) |
|  |  |  |  | —O—$CH_2$—$CH_3$ (3H) |
| $^{13}C$ | 174.8 | s |  | —C(O)— |
|  | 157.5 | s |  | DMAP |
|  | 138.4 | s |  | DMAP |
|  | 107.1 | s |  | DMAP |
|  | 66.8 | m |  | —O—$CH_2$—$(CH_2)_4$— |
|  | 60.5 | s |  | —O—$CH_2CH_3$ |
|  | 40.0 | s |  | DMAP |
|  | 34.3 | s |  | —O—$CH_2$—$CH_2$— |
|  | 30.7 | d | $^3J_{PC} = 8.1$ | $(CH_2)_3$— |
|  | 25.2 | s |  | —O—$CH_2$—$CH_2$— |
|  | 24.7 | s |  | $(CH_2)_3$— |
|  | 13.8 | s |  | —O—$CH_2$—$CH_2$— |
|  |  |  |  | $(CH_2)_3$— |
|  |  |  |  | —O—$CH_2$—$CH_2$— |
|  |  |  |  | $(CH_2)_3$— |
|  |  |  |  | —O—$CH_2$—$CH_3$ |

Example 20

$(C_2F_5)_3PF_2$. DMAP with Ethanolamine

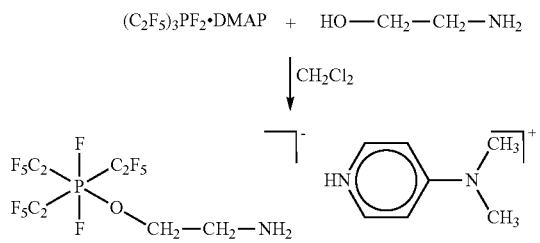

4.27 g (7.79 mmol) of $(C_2F_5)_3PF_2$. DMAP in 60 ml of dichloromethane are initially introduced in a 100 ml Schlenk flask under protective gas, and 0.48 g (7.79 mmol) of ethanolamine is added dropwise to the solution at 0° C. After the addition, the ice bath is removed, and the mixture is stirred at RT overnight. $^{19}F$- and $^{31}P$-NMR reaction checks are recorded next morning.

The reaction solution is then freed from $CH_2Cl_2$ and all volatile constituents in vacuo, leaving a slightly yellow powder.

Crude yield: 4.55 g (95.8% of theory)
NMR data: in $CD_2Cl_2$

| Nucleus | δ (ppm) | Splitting | Coupling | Assignment |
|---|---|---|---|---|
| $^{31}P$ | −148.4 | t, sept | $^1J_{PF} = 875$ | —$PF_2(C_2F_5)_3$ |
|  |  |  | $^2J_{PF} = 87$ |  |
| $^{19}F$ | −94.7 | d | $^1J_{PF} = 875$ | —$PF_2(CF_2CF_3)_3$ |
|  | −81.3 | m |  | —$PF_2(CF_2CF_3)_3$ (6F) |
|  | −80.0 | m |  | —$PF_2(CF_2CF_3)_3$ (3F) |
|  | −113.3 | m |  | —$PF_2(CF_2CF_3)_3$ (4F) |
|  | −113.5 | m |  | —$PF_2(CF_2CF_3)_3$ (2F) |
| $^1H$ | 8.00 | d | $^3J_{HH} = 5.2$ | DMAP (2H) |
|  | 7.73 | s, br |  | —$NH_2$ (2H) |
|  | 6.73 | d | $^3J_{HH} = 5.2$ | DMAP (2H) |
|  | 4.15 | m |  | —O—$(CH_2)$— |
|  | 3.19 | s |  | $NH_2$(2H) |
|  | 2.94 | m |  | DMAP (6H) |
|  | 156.7 | s |  | —O—$(CH_2)$— |
|  | 141.4 | s |  | $NH_2$(2H) |

| Nucleus | δ (ppm) | Splitting | Coupling | Assignment |
|---|---|---|---|---|
| $^{13}C$ | 106.9 | s |  | DMAP |
|  | 65.2 | m |  | DMAP |
|  | 41.8 | d |  | DMAP |
|  | 39.6 | s | $^3J_{CP} = 8.7$ | —O—$CH_2$—$CH_2$— |
|  |  |  |  | $NH_2$ |
|  |  |  |  | —O—$CH_2$—$CH_2$— |
|  |  |  |  | $NH_2$ |
|  |  |  |  | DMAP |

Note:
If the reaction is carried out in DMF instead of in $CH_2Cl_2$, another isomer forms in which the two F atoms on the phosphorus are different.

Example 21

Reaction of $(C_2F_5)_3PF_2$. DMAP with 2-methoxyethanol

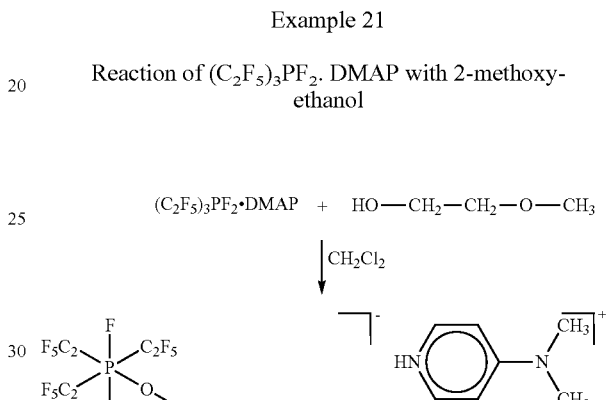

3.86 g (7.04 mmol) of $(C_2F_5)_3PF_2$. DMAP in 60 ml of dichloromethane are initially introduced in a 100 ml Schlenk flask under protective gas, and 0.54 g (7.04 mmol) of 2-methoxyethanol is added dropwise to the solution at 0° C. After the addition, the ice bath is removed, and the mixture is stirred at RT overnight. $^{19}F$- and $^{31}P$-NMR reaction checks are recorded next morning. The reaction solution is then freed from $CH_2Cl_2$ and all volatile constituents in vacuo, leaving a slightly yellow powder.

Crude yield: 4.38 g (99.8% of theory)
NMR data: in $CD_2Cl_2$

| Nucleus | δ (ppm) | Splitting | Coupling | Assignment |
|---|---|---|---|---|
| $^{31}P$ | −147.8 | t, sept | $^1J_{PF} = 878$ | —$PF_2(C_2F_5)_3$ |
|  |  |  | $^2J_{PF} = 89$ |  |
| $^{19}F$ | −94.8 | d | $^1J_{PF} = 878$ | —$PF_2(CF_2CF_3)_3$ |
|  | −81.0 | m |  | —$PF_2(CF_2CF_3)_3$ (6F) |
|  | −79.9 | m |  | —$PF_2(CF_2CF_3)_3$ (3F) |
|  | −113.2 | m |  | —$PF_2(CF_2CF_3)_3$ (4F) |
|  | −113.5 | m |  | —$PF_2(CF_2CF_3)_3$ (2F) |
| $^1H$ | 8.03 | d | $^1J_{HH} = 6.3$ | DMAP (2H) |
|  | 6.75 | d | $^1J_{HH} = 6.3$ | DMAP (2H) |
|  | 4.27 | m |  | —O—$(CH_2)_2$—O— |
|  | 3.62 | m |  | $CH_3$(2H) |
|  | 3.32 | s |  | —O—$(CH_2)_2$—O— |
|  | 3.24 | s |  | $CH_3$(2H) |
|  | 157.3 | s |  | —O—$CH_3$ |
|  | 139.3 | s |  | DMAP (6H) |
| $^{13}C$ | 106.6 | s |  | DMAP |
|  | 73.5 | d | $^3J_{CP} = 7.9$ | DMAP |
|  | 65.6 | m |  | DMAP |
|  | 57.6 | s |  | —O—$CH_2$—$CH_2$— |
|  | 40.1 | s |  | O—$CH_3$ |
|  |  |  |  | —O—$CH_2$—$CH_2$— |
|  |  |  |  | O—$CH_3$ |

-continued

| Nucleus | δ (ppm) | Splitting | Coupling | Assignment |
|---------|---------|-----------|----------|------------|
|         |         |           |          | —O—CH$_3$  |
|         |         |           |          | DMAP       |

Example 22

Reaction of $(C_2F_5)_3PF_2$ with PMe$_3$

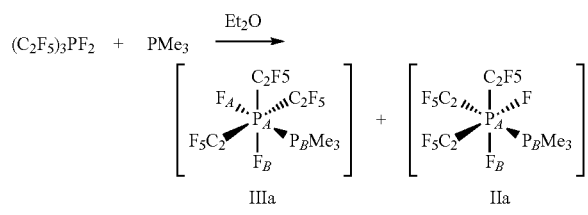

$(C_2F_5)_3PF_2$ is dissolved in diethyl ether, and excess PMe$_3$ is condensed on at −196° C. The reaction solution is warmed to room temperature and investigated by NMR spectroscopy.

$^{31}$P{$^1$H}-NMR spectroscopic data of the two conformers of [P(C$_2$F$_5$)$_3$F$_2$(PMe$_3$)] in Et$_2$O

| δ, ppm | Multiplicity | J[Hz] | Assignment |
|--------|--------------|-------|------------|
| 24.5   | d, t, quin, m | $^1$J(PP) = 302<br>$^2$J(PF) = 215<br>$^3$J(PF) = 25 | [P(C$_2$F$_5$)$_3$F$_2$(PMe$_3$)] (IIa) |
| 16.3   | m            | —     | [P(C$_2$F$_5$)$_3$F$_2$(PMe$_3$)] (IIIa) |
| −134.8 | d, d, quin, t, d | $^1$J(PF$_A$) = 923<br>$^1$J(PF$_B$) = 853<br>$^2$J(PF) = 102<br>$^2$J(PF) = 76<br>$^1$J(PP) = 53 | [P(C$_2$F$_5$)$_3$F$_2$(PMe$_3$)] (IIIa) |
| −141.9 | t, quin, t, d | $^1$J(PF) = 889<br>$^2$J(PF) = 96<br>$^2$J(PF) = 68<br>$^1$J(PP) = 303 | [P(C$_2$F$_5$)$_3$F$_2$(PMe$_3$)] (IIa) |

$^{19}$F-NMR spectroscopic data of the two conformers of [P(C$_2$F$_5$)$_3$F$_2$(PMe$_3$)] in Et$_2$O

| δ, ppm | Multiplicity | J[Hz] | Assignment | Integral |
|--------|--------------|-------|------------|----------|
| −28.6  | d, d, m      | $^1$J(P$_A$F) = 885<br>$^2$J(P$_B$F) = 215 | PF (IIa) | 2.2 |
| −29.6  | d, m         | $^1$J(P$_A$F) = 923 | PF$_A$ (IIIa) | 3.3 |
| −60.0  | d, d, m      | $^1$J(P$_A$F) = 853<br>$^2$J(P$_B$F) = 140 | PF$_B$ (IIIa) | 3.7 |
| −81.3  | m            | —     | —          | 14.1 |
| −81.7  | m            | —     | —          | 16.2 |
| −82.4  | m            | —     | —          | 37.5 |
| −103.9 | m            | —     | —          | 9.8  |
| −104.6 | m            | —     | —          | 4.5  |
| −105.7 | m            | —     | —          | 8.9  |
| −106.4 | m            | —     | —          | 3.2  |
| −107.5 | m            | —     | —          | 0.5  |
| −110.6 | m            | —     | —          | 8.5  |
| −114.7 | m            | —     | —          | 4.3  |

Example 23

Reaction of $(C_2F_5)_2PF_3$ with PMe$_3$

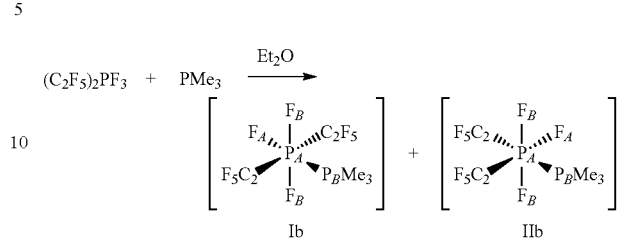

$(C_2F_5)_2PF_3$ is dissolved in diethyl ether, and excess PMe$_3$ is condensed on at −196° C. The reaction solution is warmed to room temperature and investigated by NMR spectroscopy.

$^{31}$P{$^1$H}-NMR spectroscopic data of the two conformers of [P(C$_2$F$_5$)$_2$F$_3$(PMe$_3$)] in Et$_2$O

| δ, ppm | Multiplicity | J[Hz] | Assignment |
|--------|--------------|-------|------------|
| 19.5   | d, d, t, m   | $^1$J(PP) = 463<br>$^2$J(PF$_A$) = 268<br>$^2$J(PF$_B$) = 147 | [P(C$_2$F$_5$)$_2$F$_3$(PMe$_3$)] (IIb) |
| 10.9   | m            | —     | [P(C$_2$F$_5$)$_2$F$_3$(PMe$_3$)] (Ib) |
| −139.2 | d, t, d, quin | $^1$J(PF$_A$) = 907<br>$^1$J(PF$_B$) = 956<br>$^1$J(PP) = 71<br>$^2$J(PF) = 118 | [P(C$_2$F$_5$)$_2$F$_3$(PMe$_3$)] (Ib) |
| −140.0 | d, t, d, m   | $^1$J(PF$_A$) = 949<br>$^1$J(PF$_B$) = 947<br>$^1$J(PP) = 465<br>$^2$J(PF) = 104 | [P(C$_2$F$_5$)$_2$F$_3$(PMe$_3$)] (IIb) |

$^{19}$F-NMR spectroscopic data of the two conformers of [P(C$_2$F$_5$)$_2$F$_3$(PMe$_3$)] in Et$_2$O

| δ, ppm | Multiplicity | J[Hz] | Assignment | Integral |
|--------|--------------|-------|------------|----------|
| −21.9  | d, d, m      | $^1$J(P$_A$F) = 945<br>$^2$J(P$_B$F) = 268 | PF$_A$ (IIb) | 0.3 |
| −48.6  | d, m         | $^1$J(PF) = 907 | PF$_A$ (Ib) | 1 |
| −70.5  | d, d, m      | $^1$J(PF) = 957<br>$^2$J(FF) = 92 | PF$_B$ (Ib) | 2 |
| −72.2  | d, d, d, m   | $^1$J(PF) = 948<br>$^2$J(PF) = 146<br>$^2$J(FF) = 55 | PF$_B$ (IIb) | 0.8 |
| −80.4  | m            | —     | CF$_3$ (IIb) | 1 |
| −82.0  | d, quar, d   | $^3$J(PF) = 21<br>$^4$J(FF) = 5<br>$^4$J(P$_B$F) = 1 | CF$_3$ (Ib) | 6 |
| −82.4  | m            | —     | CF$_3$ (IIb) | 1.1 |
| −112.5 | d, quar      | $^2$J(PF) = 119<br>$^3$J(FF) = 15 | CF$_2$ (Ib) | 4 |
| −117.0 | d, m         | $^2$J(PF) = 95 | CF$_2$ (IIb) | — |
| −118.1 | d, m         | $^2$J(PF) = 105 | CF$_2$ (IIb) | — |

The invention claimed is:

1. A compound formula I

[P(R$_f$)$_n$F$_{5-n}$D]$^-$     I, where

R$_f$ in each case, independently of one another, denotes a straight-chain or branched fluoroalkyl group having 1 to 8 C atoms, n denotes 1, 2 or 3 and D denotes a Lewis base selected from triphenylphosphine oxide, trimethyl phosphate, aromatic amines, dialkyl ethers, aromatic or aliphatic tertiary phosphines, dialkylformamides, dialkylacetamides or N-alkyl-2-pyrrolidones, where said alkyl groups have, in each case independently of one another, 1 to 8 C atoms, or
a tautomer or stereoisomer thereof, including mixtures thereof in all ratios.

2. A compound according to claim 1, wherein D denotes an aromatic amine, a dialkyl ether, an aromatic or aliphatic tertiary phosphine, a dialkylformamide, a dialkylacetamide or an N-alkyl-2-pyrrolidone, where said alkyl groups have, in each case independently of one another, 1 to 8 C atoms.

3. A compound according to claim 1, wherein D denotes 4-dimethylaminopyridine or dimethylformamide.

4. A process for the preparation of compounds according to claim 1, said process comprising:
reacting a fluoroalkylfluorophosphorane of formula II $(R_f)_n PF_{5-n}$   II, where
$R_f$ in each case, independently of one another, denotes a straight-chain or branched fluoroalkyl group having 1 to 8 C atoms and
n denotes 1, 2 or 3,
with a Lewis base D selected from triphenylphosphine oxide, trimethyl phosphate, aromatic amines, dialkyl ethers, aromatic or aliphatic tertiary phosphines, dialkylformamides, dialkylacetamides or N-alkyl-2-pyrrolidones, where said alkyl groups have, in each case independently of one another, 1 to 8 C atoms.

5. The process according to claim 4, wherein the perfluoroalkylfluoro-phosphorane is employed in excess.

6. A method for masking at least one OH group of an organic compound, comprising: reacting an organic compound having at least one OH group with a compound according to claim 1.

7. The method according to claim 6, wherein the organic compound having at least one OH group is an aliphatic or aromatic alcohol containing at least one OH group or is an oligomeric or polymeric compound containing at least one OH group.

8. The method according to claim 6, wherein the compound having at least one OH group is a polyol or a polyethylene glycol.

9. The method according to claim 7, wherein the compound having at least one OH group is a polyol or a polyethylene glycol.

10. The process according to claim 4, wherein the Lewis base is employed in excess.

11. A compound according to claim 1, wherein Lewis base D is triphenylphosphine oxide or trimethyl phosphate.

12. A compound according to claim 1, wherein Lewis base D is tri-phenylphosphine, diphenylmethylphosphine, trimethylphosphine, triethylphosphine, tri-i-propylphosphine, tributylphosphine, trihexylphosphine, or tri-cyclohexylphosphine.

13. A compound according to claim 1, wherein Lewis base D is trimethylphosphine.

14. A compound according to claim 1, wherein Lewis base D is dimethyl-formamide, diethylformamide, or dipropylformamide.

15. A compound according to claim 1, wherein Lewis base D is dimethylformamide.

16. A compound according to claim 1, wherein Lewis base D is dimethylacetamide, diethylacetamide, or dipropylacetamide.

17. A compound according to claim 1, wherein Lewis base D is N-methyl-2-pyrrolidone, N-ethyl-2-pyrrolidone, N-propyl-2-pyrrolidone, or N-butyl-2-pyrrolidone.

18. A compound according to claim 1, wherein Lewis base D is an aromatic amine or dialkylformamide.

19. A compound according to claim 1, wherein Lewis base D is 4-dimethylaminopyridine.

20. A compound according to claim 1, wherein $R_f$ is $CF_3$—CHF—$CF_2$-, $CF_2H$—$CF_2$—, $CF_3$—$CF_2$—$CH_2$—, $CF_3$—$CF_2$—$CH_2$—$CH_2$—, $CF_3$—$CF_2$—$CF_2$—$CF_2$—$CF_2$—$CF_2$—$CH_2$—$CH_2$—, trifluoromethyl, pentafluoroethyl, heptafluoropropyl, heptafluoroisopropyl, n-nonafluorobutyl, sec-nonafluorobutyl, tert-nonafluoro-butyl, dodecafluoropentyl, 1-, 2- or 3-trifluoromethyloctafluorobutyl, 1,1-, 1,2- or 2,2-bis(trifluoromethyl)pentafluoropropyl, 1-pentafluoroethylhexafluoropropyl, n-tridecafluorohexyl, n-pentadecafluoroheptyl, or n-heptadecafluorooctyl.

* * * * *